(12) United States Patent
Debrauwer et al.

(10) Patent No.: US 12,043,596 B2
(45) Date of Patent: Jul. 23, 2024

(54) THERMOCHROMIC PIGMENT COMPOSITIONS

(71) Applicant: SOCIETE BIC, Clichy (FR)

(72) Inventors: Christelle Debrauwer, Saint Germain sur Morin (FR); Anne-Lise Damiano, Lagny sur Marne (FR); Alexander Bourque, Montevrain (FR); Francois Foulonneau, Bordeaux (FR); Guillaume Chollet, Leognan (FR)

(73) Assignee: SOCIETE BIC, Clichy (FR)

( * ) Notice: Subject to any disclaimer, the term of this patent is extended or adjusted under 35 U.S.C. 154(b) by 1078 days.

(21) Appl. No.: 16/608,452

(22) PCT Filed: Apr. 24, 2018

(86) PCT No.: PCT/FR2018/051031
§ 371 (c)(1),
(2) Date: Jan. 6, 2020

(87) PCT Pub. No.: WO2018/197807
PCT Pub. Date: Nov. 1, 2018

(65) Prior Publication Data
US 2020/0207699 A1 Jul. 2, 2020

(30) Foreign Application Priority Data
Apr. 27, 2017 (FR) ...................... 1753677

(51) Int. Cl.
*C07C 69/616* (2006.01)
*C07C 43/205* (2006.01)
(Continued)

(52) U.S. Cl.
CPC .......... *C07C 69/616* (2013.01); *C07C 43/205* (2013.01); *C07C 69/34* (2013.01);
(Continued)

(58) Field of Classification Search
CPC ..... C07C 69/616; C07C 43/205; C09D 11/00; C09D 11/17; C09D 11/18; C09D 11/50
(Continued)

(56) References Cited

U.S. PATENT DOCUMENTS

| 2,503,701 A | 4/1950 | Mortimer |
| 4,720,301 A | 1/1988 | Tsutomu et al. |
| 2005/0090593 A1* | 4/2005 | Heuer ................. C07C 43/315 524/366 |

FOREIGN PATENT DOCUMENTS

| EP | 3009493 A1 | 4/2016 |
| WO | 2016198784 A1 | 12/2016 |

OTHER PUBLICATIONS

International Search Report dated Aug. 16, 2018 in related PCT application No. PCT/FR2018/051032, 2 pages.
(Continued)

*Primary Examiner* — James E McDonough
(74) *Attorney, Agent, or Firm* — Ruggiero, McAllister & McMahon LLC

(57) ABSTRACT

A thermochromic pigment composition including compounds of formula (I):

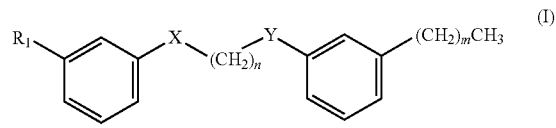

in which: X represents $CHR_2$, O, OCO or CH=CH; Y represents O, COO, or OCOO; $R_1$ represents H or $(CH_2)_p CH_3$; $R_2$ represents phenyl or H; m=12-18; n=0-14; p=12-18; and on the condition that, if n=0, X represents $CHR_2$ or CH=CH.

(Continued)

The thermochromic pigment compositions having compounds of formula (I), include thermochromic pigment microcapsules. The thermochromic pigment capsules are useable for thermochromic pigment compositions in ink which may be used writing instruments.

12 Claims, 1 Drawing Sheet

(51) Int. Cl.
    *C07C 69/34*     (2006.01)
    *C09D 11/17*     (2014.01)
    *C09D 11/18*     (2006.01)
    *C09D 11/50*     (2014.01)

(52) U.S. Cl.
    CPC .............. *C09D 11/17* (2013.01); *C09D 11/18* (2013.01); *C09D 11/50* (2013.01)

(58) Field of Classification Search
    USPC ...... 16/31.01, 31.13, 31.6, 31.64; 106/31.01, 106/31.13, 31.6, 31.64
    See application file for complete search history.

(56) References Cited

OTHER PUBLICATIONS

International Search Report dated Aug. 23, 2018 in related PCT application No. PCT/FR2018/051033, 2 pages.
Amorati et al, "Synthesis of new Cardonal and Cardo derivatives by allylation and regioselctive cyclocarbonylation reactions", Synthesis, No. 18, Jan. 1, 2002, Georg Thieme Verlag, Stuttgart, DE, pp. 2749-2755.
Kaufmann et al, "To know the Cashew-ole II about some derivatives of the main components of the shell folk". Jan. 1, 1967 (Jan. 1, 1967). pp. 577-579.
International Search Report dated Aug. 10, 2018 for PCT application No. PCT/FR2018/051031.

* cited by examiner

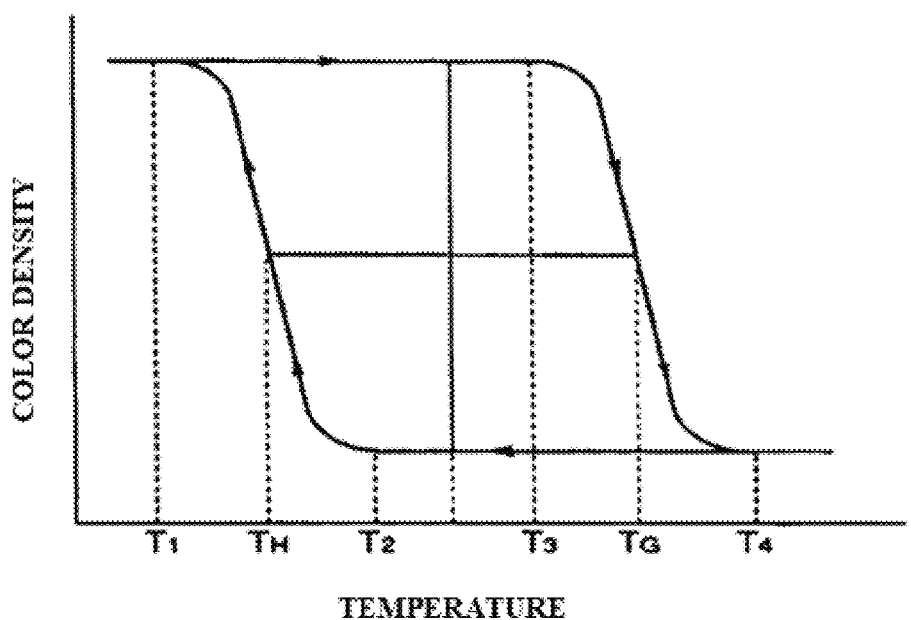

THERMOCHROMIC PIGMENT COMPOSITIONS

CROSS REFERENCE TO RELATED APPLICATIONS

This application is a National Stage application of International Application No. PCT/FR2018/051031, filed on Apr. 24, 2018, now published as WO/2018/197807 and which claims priority to French Application No. 1753677, filed Apr. 27, 2017, the entire contents of which is incorporated herein by reference.

FIELD

The present disclosure relates to novel compounds and to use thereof as a reaction medium in thermochromic pigment compositions. The present disclosure also provides thermochromic pigment microcapsules comprising such thermochromic pigment compositions, ink compositions comprising such thermochromic pigment microcapsules, and finally writing instruments comprising such ink compositions.

DESCRIPTION OF RELATED ART

Thermochromic pigment compositions have reversible discoloration properties associated with changes in temperature. These compositions are employed when an ink marking needs to be erased repeatedly.

The thermochromic effect of an ink works through the combination of the following three compounds:
(A) at least one organic electron-donor dye or leuco dye compound,
(B) at least one electron-acceptor or color-developer compound, and
(C) at least one compound serving as a reaction medium that is capable of leading to a reversible electron-accepting/donating reaction attributable to compounds (A) and (B) or thermochromic regulating agent.

Temperature changes reversibly bring about the coloration or discoloration of the inks. Thus, an increase in heat will result in erasure of the ink, whereas cooling will cause it to appear. These changes follow the diagram of FIG. 1. In this diagram, the temperature at which the ink begins to disappear is T3, the temperature at which the color of the ink has completely disappeared is T4, and TG is the mean temperature between T3 and T4. Conversely, the temperature at which the color of the ink begins to reappear is T2, the temperature at which the color of the ink has completely reappeared is T1, and TH is the temperature in the middle between T1 and T2. The range between (TH) and (TG) is referred to as the color change hysteresis width (ΔH).

SUMMARY

The present disclosure relates to compounds that enable thermochromic pigment microcapsules to be prepared that have optimal melting and crystallization temperature ranges corresponding respectively to the discoloration and recoloration temperatures of these compositions. The compounds when used as a thermochromic regulating agent in thermochromic inks: They exhibit remarkable hysteresis characteristics and an extremely high color contrast between the colored state and the discolored state. The compounds also can be prepared by means of an ecological process, i.e., from a recycled and biosourced product, 3-pentadecylphenol, which originates from the waste products of cashew nut production.

BRIEF DESCRIPTION OF THE DRAWING

An embodiment of the related art is described herein with reference to the following FIGURE.

FIG. 1 is a plot of temperature versus color density for a thermochromatic pigment of the related art.

DETAILED DESCRIPTION

According to a first aspect, the object of the present disclosure is a compound corresponding to the following formula (I):

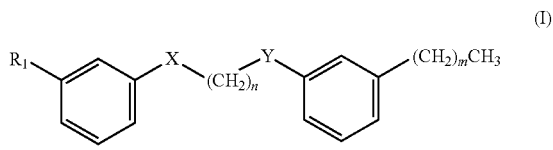

in which:
X represents $CHR_2$, O, OCO, or CH=CH,
Y represents O or COO,
$R_1$ represents H or $(CH_2)_p CH_3$,
$R_2$ represents a phenyl group or H,
m=12-18,
n=0-14,
p=12-18, and
on the condition that, if n=0, X represents $CHR_2$ or CH=CH.

In terms of the present disclosure:
if X=OCO: the oxygen atom is attached to the phenyl group and the carbonyl group to the $(CH_2)_n$ chain, and
if Y=COO: the carbonyl group is attached to the $(CH_2)_n$ chain and the oxygen atom to the phenyl group.

In formula (I) above, X is selected from among $CHR_2$, O, or OCO.

In formula (I) above, m can be selected independently from among the following integers: 12, 13, 14, 15, 16, 17, or 18.

In formula (I) above, n can be selected independently from among the following integers: 0, 1, 2, 3, 4, 5, 6, 7, 8, 9, 10, 11, 12, 13, or 14.

In formula (I) above, p can be selected independently from among the following integers: 12, 13, 14, 15, 16, 17, or 18.

In formula (I) above, n=0-10.
In formula (I) above, p=14.
The compound of formula (I) is a compound in which:
X represents $CHR_2$, O, or OCO,
Y represents O or COO,
$R_1$ represents H or $(CH_2)_p CH_3$,
$R_2$ represents a phenyl group or H,
m=12-18, and
n=0-14, or n=0-10,
p=12-18, or p=14,
on the condition that, if n=0, X represents $CHR_2$.

According to a first embodiment, the compound corresponds to the following formula ($I_a$):

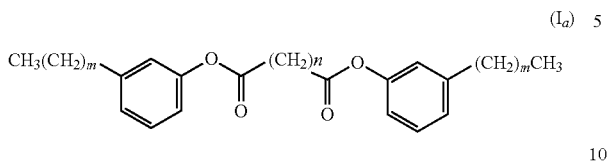

($I_a$)

in which:
m=12-18, and
n=1-14, or n=1-10,
  in formula ($I_a$): m=14,
  in formula ($I_a$): n=8.

According to a second embodiment, the compound corresponds to the following formula ($I_b$):

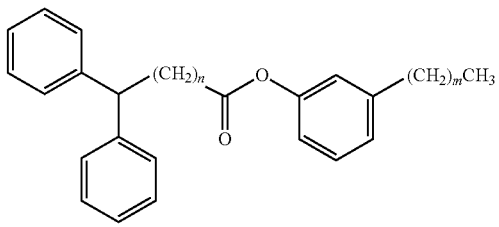

($I_b$)

in which:
m=12-18, and
n=0-14, or n=0-10,
  in formula ($I_b$): m=14,
  in formula ($I_b$): n=1.

According to a third embodiment, the compound corresponds to the following formula ($I_c$):

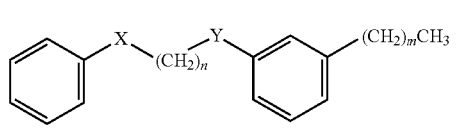

($I_c$)

in which:
X represents $CH_2$, O, or CH=CH,
Y represents O or COO,
m=12-18, and
n=1-14, or n=1-10, or n=1-8,
  in formula ($I_c$): m=14,
  in formula ($I_c$): n=2.

The compounds of formula ($I_a$), ($I_b$), and ($I_c$) can be synthesized according to the first two synthetic routes described below. The compound of formula ($I_c$) can also be synthesized according to the third synthetic route described below.

The first synthetic route corresponds to the following reaction scheme:

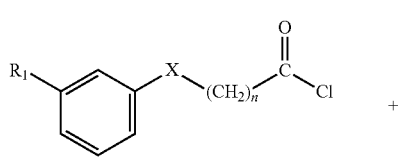

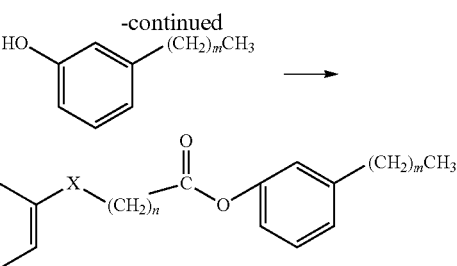

In this first synthetic route, alcohol acts as a solvent. It is used in excess, or at an alcohol/carboxylic acid ratio of 1.5/1 to 3/1, or of 2/1. The mixture of alcohol and carboxylic acid is heated to a temperature ranging from 120 to 200° C., or from 140 to 160° C., under reduced pressure, or between 200 and 800 mbar, until the acid is completely consumed. The mixture is heated under reduced pressure for a period ranging from 1 to 4 days. The compound of formula ($I_a$), ($I_b$), or ($I_c$) obtained is then purified by recrystallization.

The second synthetic route corresponds to the following reaction scheme:

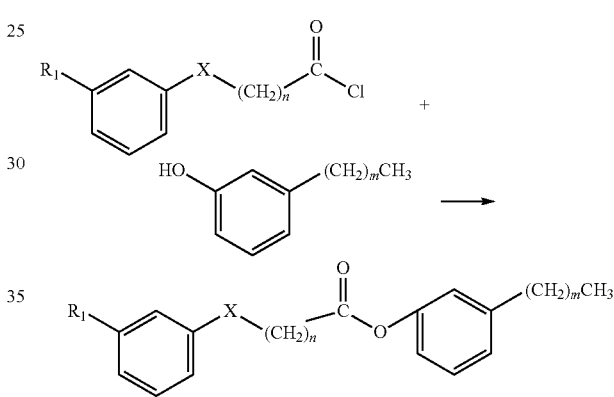

In this second synthetic route, the phenol is solubilized with a catalyst in an aprotic polar solvent such as tetrahydrofuran (THF). The catalyst is a volatile base such as triethylamine. The mixture is kept cold at a temperature ranging from −20 to 30° C., or from 0 to 20° C. The mixture is kept cold in an ice bath or in a solid $CO_2$ bath immersed in a solvent such as acetone or ethanol. The mixture is rendered inert by adding nitrogen. The acid chloride is then slowly added dropwise over a period of 15 to 60 minutes. The phenol/acid chloride ratio used is 1.1/1 to 1/1.1, or 1/1. The temperature of the mixture is then raised to room temperature (25° C.), and the mixture is maintained at this temperature for 1 to 3 hours, preferably 2 hours, under stirring. The compound of formula ($I_a$), ($I_b$), or ($I_c$) obtained is then purified by recrystallization.

The compound of formula ($I_c$) can also be synthesized according to the following synthetic route:

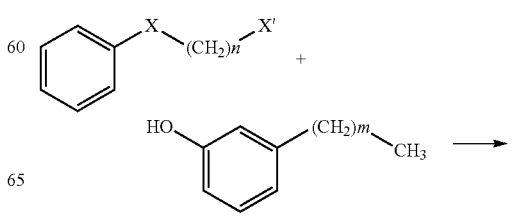

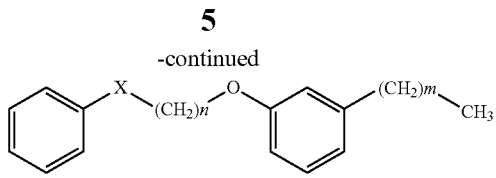

where the substituent X' represents a halogen atom selected from among Cl, Br, I, or F, and preferably the Br atom.

In this synthetic route, the compounds of formula ($I_c$) can be prepared:

Either by solubilization of the reagents in a polar solvent such as tert-butanol in the presence of a strong base such as sodium hydroxide. The alcohol/halogenated compound ratio used is 1/1 to 1.4/1, or 1.2/1. The reagent mixture is heated under reflux at 75 to 90° C. for 2 to 10 hours, preferably 6 hours. The compound of formula ($I_c$) obtained is then purified by recrystallization Or by solubilization of the reagents in a polar solvent such as acetonitrile in the presence of a strong base such as potassium carbonate. The alcohol/halogenated compound ratio used is 1/1 to 1.4/1, or 1.2/1. The reagent mixture is heated under reflux at a temperature of 75 to 90° C. for 5 to 10 days, preferably 7 days. The mixture is then filtered in order to remove the weak base. The compound of formula ($I_c$) obtained is then purified by recrystallization.

The compound of formula (I) is chosen from among the following compounds:

(1)
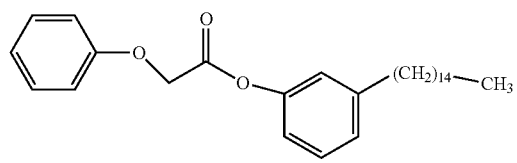

(2)
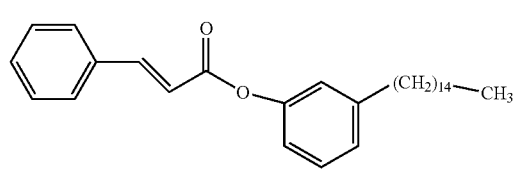

(3)
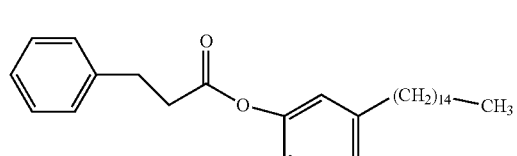

(4)
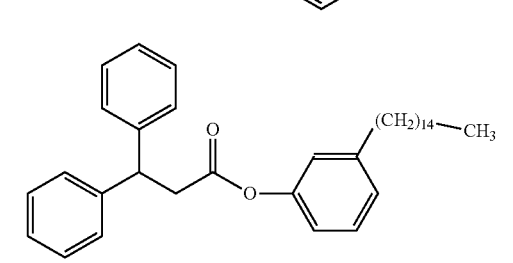

(5)
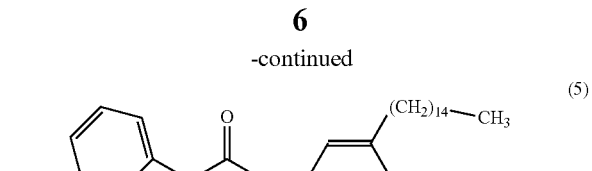

(6)
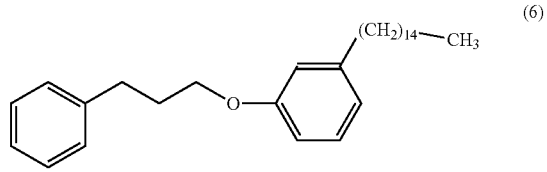

(7)
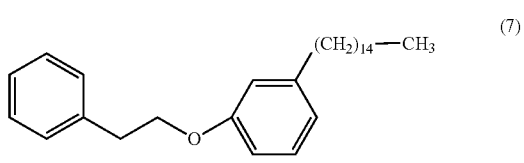

(8)
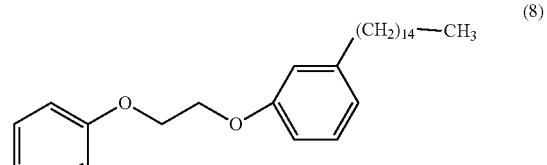

(9)
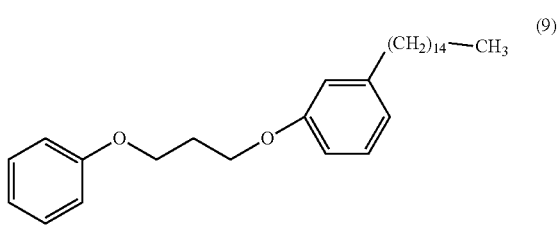

(10)
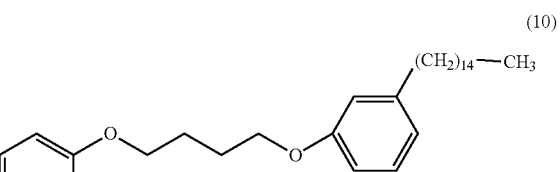

(11)
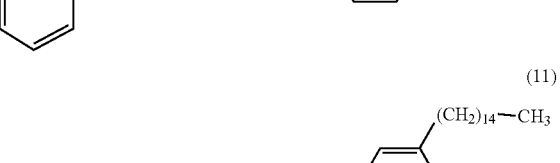

(12)
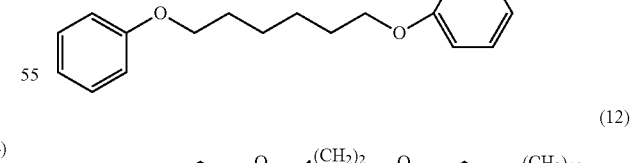

(13)
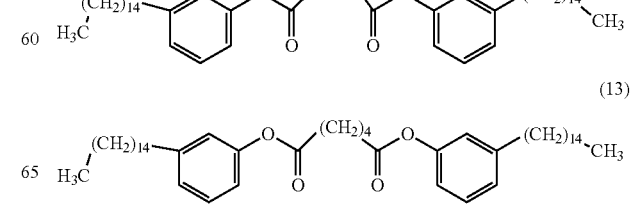

-continued

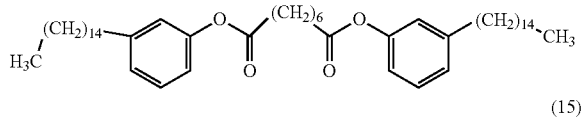

(14)

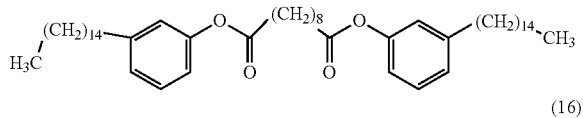

(15)

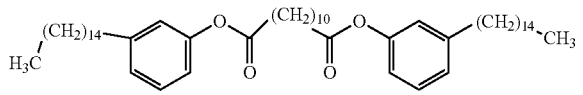

(16)

The melting temperature of the compound of formula (I) can vary from 20 to 80° C., or from 30 to 80° C., or from 40 to 70° C. It is this optimum melting temperature that makes the compound of formula (I) an ideal compound that has the properties required for use as a thermochromic regulating agent in thermochromic pigment compositions.

Therefore, another object of the disclosure is a thermochromic pigment composition comprising:
(A) at least one organic electron-donor dye or leuco dye compound,
(B) at least one electron-acceptor or color-developer compound, and
(C) at least one compound of formula (I) as defined according to the disclosure.

The weight ratios of compounds (A), (B), and (C) are influenced by the nature and concentration of each of these compounds.

The weight ratio of organic electron-donating dye compound (A) can vary from 1 to 10%, or from 1 to 6%, or from 2 to 4%, by weight relative to the total weight of the thermochromic pigment composition.

The weight ratio of electron-accepting compound (B) can vary from 1 to 20%, or from 1 to 14%, or from 4 to 10%, by weight relative to the total weight of the thermochromic pigment composition.

The weight ratio of compound (C) of formula (I) acting as a reaction medium can vary from 70 to 98%, or from 80 to 98%, or from 86 to 94%, by weight relative to the total weight of the thermochromic pigment composition.

Therefore, the thermochromic pigment composition may comprise:
(A) from 1 to 10%, or from 1 to 6%, or from 2 to 4%, by weight of at least one organic electron-donating dye compound,
(B) from 1 to 20%, or from 1 to 14%, or from 4 to 10%, by weight of at least one electron-accepting compound, and
(C) from 70 to 98%, or from 80 to 98%, or from 86 to 94%, by weight of at least one compound of formula (I).

The thermochromic pigment composition comprises:
(A) from 2 to 4% by weight of at least one organic electron-donating dye compound,
(B) from 4 to 10% by weight of at least one electron-accepting compound, and
(C) from 86 to 94% by weight of at least one compound of formula (I).

The thermochromic pigment composition has a color change hysteresis width ($\Delta H$) after encapsulation ranging from 20 to 80° C., or from 30 to 80° C., or from 40 to 70° C.

Some noteworthy organic electron-donating dye compounds (A) include conventionally known compounds such as diphenylmethane phthalides, phenylindolyl phthalides, indolyl phthalides, diphenylmethane azaphthalides, phenylindolyl azaphthalides, fluoranes, styrylquinolines, and diazarhodamine lactones, with examples of these compounds being presented hereinafter.

The organic electron-donating dye compound (A) can thus be chosen from 3-(4-diethylamino-2-ethoxyphenyl)-3-(1-ethyl-2-methylindol-3-yl)-4-azaphthalide (Blue 63, CAS no.: 69898-40-4), 3,3-bis(p-dimethylaminophenyl)-6-dimethylaminophthalate (CAS no.: 1552-42-7), 2'-chloro-6'-(diethylamino)-3'-methylfluorane (CAS no.: 21121-62-0), 6'-(diethylamino)-1',3'-dimethylfluorane (CAS no.: 21934-68-9), 2-chloro-6-(diethylamino)-fluorane (CAS no.: 26567-23-7), 3-diethylaminobenzofluorane (CAS no.: 26628-47-7), 3',6'-bis(diethylamino)-2-(4-nitrophenyl)spiro[isoindole-1,9'-xanthene]-3-one (CAS no.: 29199-09-5), 2-phenylamino-3-methyl-6-diethylaminofluorane (CAS no.: 29512-49-0), 2'-(dibenzylamino)-6'-(diethylamino)fluorane (CAS no.: 34372-72-0), 2-(2,4-dimethylphenylamino)-3-methyl-6-diethylaminofluorane (CAS no.: 36431-22-8), 3-(1,2-dimethyl-3-indolyl)-3-[4-(diethylamino)-2-methylphenyl]phthalide (CAS no.: 36499-49-7), 3',6'-dimethoxyfluorane (CAS no.: 36886-76-7), 3,3-bis-(1-butyl-2-methyl-indol-3-yl)-3H-isobenzofuran-1-one (Red 40, CAS no.: 50292-91-6), 3,3-bis-(2-methyl-1-octyl-1H-indol-3-yl)-3H-isobenzofuran-1-one (CAS no.: 50292-95-0), 2'-anilino-6'-[ethyl(p-tolyl)amino]-3'-methylspiro[isobenzofuran-1 (3H),9'-[9H]xanthene]-3-one (CAS no.: 59129-79-2), 3-(N-ethyl-n-isopentylamino)-6-methyl-7-anilino fluorene (CAS no.: 70516-41-5), 3-[4-(diethylamino)phenyl]-3-(1-ethyl-2-methyl-1H-indol-3-yl)phthalide (CAS no.: 75805-17-3), 2'-(2-chloroanilino)-6'-(dibutylamino)fluorane (CAS no.: 82137-81-3), 2-phenylamino-3-methyl-6-dibutylaminofluorane (CAS no.: 89331-94-2), 3-(1-butyl-2-methyl-1H-indol-3-yl)-6-(dimethylamino)-3-[4-(dimethylamino)phenyl]-3-(1 (3H)-isobenzofuranone (CAS no.: 92453-31-1), 7-(4-diethylamino-2-hexyloxyphenyl)-7-(1-ethyl-2-methyl-1H-indol-3-yl)-7H-furo[3,4-b]pyridine-5-one (Blue 203, CAS no.: 98660-18-5), 7,7-bis[4-(diethylamino)-2-ethoxyphenyl]furo[3,4-b]pyridine-5-one (CAS no.: 132467-74-4), N,N-dimethyl-4-[2-[2-(octyloxy)phenyl]-6-phenyl-4-pyridinyl]benzenamine (Yellow CK37, CAS no.: 144190-25-0), 3-(2,2-bis(1-ethyl-2-methylindol-3-yl)vinyl)-3-(4-diethylaminophenyl)-phthalide (CAS no.: 148716-90-9).

Preferably, the organic electron-donating dye compound (A) is selected from among 3-(4-diethylamino-2-ethoxyphenyl)-3-(1-ethyl-2-methylindol-3-yl)-4-azaphthalide (Blue 63, CAS no.: 69898-40-4), 2'-(dibenzylamino)-6'-(diethylamino)fluorane (CAS no.: 34372-72-0), N,N-dimethyl-4-[2-[2-(octyloxy)phenyl]-6-phenyl-4-pyridinyl]benzenamine (Yellow CK37, CAS no.: 144190-25-0), 7-(4-diethylamino-2-hexyloxyphenyl)-7-(1-ethyl-2-methyl-1H-indol-3-yl)-7H-furo[3,4-b]pyridine-5-one (Blue 203, CAS no.: 98660-18-5), 2-(2,4-dimethylphenylamino)-3-methyl-6-diethylaminofluoran (Black 15, CAS no.: 36431-22-8), and 3,3-bis-(1-butyl-2-methyl-indol-3-yl)-3H-isobenzofuran-1-one (Red 40, CAS no.: 50292-91-6).

Some noteworthy electron-accepting compounds (B) include but are not limited to compounds having an active proton, such as compounds having a phenolic hydroxyl group (monophenols or polyphenols), and derivatives thereof having substituents such as alkyl group, an aryl group, an acyl group, an alkoxycarbonyl group, a carboxy group, esters thereof, an amido group or a halogen atom, and phenol-aldehyde condensed resins such as bisphenols or trisphenols.

In terms of the present disclosure:

"Alkyl" refers to a saturated, linear or branched, hydrocarbon aliphatic group in $C_1$-$C_{20}$, in $C_1$-$C_{12}$, in $C_1$-$C_6$, or in $C_1$-$C_4$. The term "branched" means that at least one lower alkyl group such as methyl or ethyl is carried by a linear alkyl chain. Some noteworthy alkyl groups include methyl, ethyl, n-propyl, i-propyl, n-butyl, t-butyl, and n-pentyl groups.

"Aryl" refers to any functional group or substituent derived from at least one aromatic ring; an aromatic cycle corresponds to any mono- or polycyclic group plane containing a delocalized n system in which each atom of the cycle has an orbital p, said orbitals p overlapping one another; noteworthy aryl groups of this kind include phenyl, biphenyl, naphthalene, and anthracene groups. The aryl groups comprise from 4 to 12 carbon atoms, or from 5 to 6 carbon atoms. The aryl group is a phenyl group.

Therefore, the electron-accepting compound (B) can be selected from among 2,2-bis(4-hydroxy-3-methylphenyl) propane (Bisphenol C, CAS no.: 79-97-0), 4-hexyl-1,3-dihydroxybenzene (4-hexylresorcinol, CAS no.: 136-77-6), 4,4'-cyclohexylidenebisphenol (BPZ, CAS no.: 843-55-0), 4,4'-(hexafluoroisopropylidene)diphenol (Bisphenol AF, CAS no.: 1478-61-1), 4,4'-(1-phenylethylidene)bisphenol (CAS no.: 1571-75-1), 2,2'-dihydroxybiphenyl (CAS no.: 1806-29-7), 4,4'-ethylidenebisphenol (CAS no.: 2081-08-5), 4,4'-(1,4-phenylenediisopropylidene)bisphenol (CAS no.: 2167-51-3), 1,1-bis(4-hydroxy-3-methylphenyl)cyclohexane (CAS no.: 2362-14-3), 9,9-bis(4-hydroxyphenyl) fluorene (CAS no.: 3236-71-3), 4,4'-(1,3-phenylenediisopropylidene)bisphenol (CAS no.: 13595-25-0), 1,1,1-tris(4-hydroxyphenyl)ethane (CAS no.: 27955-94-8), 4,4'-(2-ethylhexylidene)diphenol (CAS no.: 74462-02-5), $\alpha,\alpha,\alpha'$-tris(4-hydroxyphenyl)-1-ethyl-4-isopropylbenzene (CAS no.: 110726-28-8), 4-(1,1,3,3-tetramethylbutyl)phenol (CAS no.: 140-66-9), 4-hydroxydiphenylether (CAS no.: 831-82-3), bis(2-hydroxy-1-naphthyl)methane (CAS no.: 1096-84-0), 4-(methylsulfonyl)phenol (CAS no.: 14763-60-1), 4-hydroxyphenyl-4'-isopropoxyphenyl sulfone (CAS no.: 95235-30-6), 4,4'-dihydroxybiphenyl (CAS no.: 92-88-6), 4-hydroxybiphenyl (CAS no.: 92-69-3), p-hydroxycumene (CAS no.: 99-89-8), 2,4-dihydroxybenzophenone (CAS no.: 131-56-6), l'hydroquinone monomethylether (MEHQ, CAS no.: 150-76-5), 3-n-pentadecylphenol (CAS no.: 501-24-6), 4-(2-phenylisopropyl)phenol (CAS no.: 599-64-4), 5-chloro-2-(2,4-dichlorophenoxy)phenol (CAS no.: 3380-34-5), N-(p-toluenesulfonyl)-N'-(3-(p-toluenesulfonyloxy)phenyl)urea (CAS no.: 232938-43-1), 2,2-bis(3,5-dibromo-4-hydroxyphenyl)propane (CAS no.: 79-94-7), 4,4'-isopropylidenediphenol (CAS no.: 80-05-7), and 4,4'-sulfonyldiphenol, (BPS, CAS no.: 80-09-1).

Preferably, the electron-accepting compound (B) is selected from among 2,2-bis(4-hydroxy-3-methylphenyl) propane (Bisphenol C, CAS no.: 79-97-0), 4-hexyl-1,3-dihydroxybenzene (4-hexylresorcinol, CAS no.: 136-77-6), 4,4'-cyclohexylidenebisphenol (BPZ, CAS no.: 843-55-0), 4,4'-(hexafluoroisopropylidene)diphenol (Bisphenol AF, CAS no.: 1478-61-1), 4,4'-(1-phenylethylidene)bisphenol (CAS no.: 1571-75-1), 2,2'-dihydroxybiphenyl (CAS no.: 1806-29-7), 4,4'-(1,4-phenylenediisopropylidene)bisphenol (CAS no.: 2167-51-3), 1,1-bis(4-hydroxy-3-methylphenyl) cyclohexane (CAS no.: 2362-14-3), 9,9-bis(4-hydroxyphenyl)fluorene (CAS no.: 3236-71-3), 4,4'-(1,3-phenylenediisopropylidene)bisphenol (CAS no.: 13595-25-0), 1,1,1-tris(4-hydroxyphenyl)ethane (CAS no.: 27955-94-8), 4,4'-(2-ethylhexylidene)diphenol (CAS no.: 74462-02-5), and $\alpha,\alpha,\alpha'$-tris(4-hydroxyphenyl)-1-ethyl-4-isopropylbenzene (CAS no.: 110726-28-8).

The thermochromic pigment composition is prepared by dissolving compounds (A) and (B) in compound (C) of formula (I), followed by stirring until a homogeneous mixture is obtained using an agitator such as a homo-mixer or disperser.

Compounds (A) and (B) combined in this manner with the compound of formula (I) can be formulated as microcapsules. The thermochromic pigment composition encapsulated in microcapsules to form thermochromic pigment microcapsules. Such thermochromic pigment microcapsules constitute another object of the disclosure. They have characteristics in as much as they are resistant to mechanical stresses, insoluble and therefore dispersible in water, and slow to agglomerate.

The melting temperature (or discoloration temperature T4) of the thermochromic pigment microcapsules of the disclosure can vary from 20 to 80° C., or from 30 to 80° C., or from 40 to 70° C.

The crystallization temperature (or recoloration temperature T1) of the thermochromic pigment microcapsules can vary from −40 to 20° C., or from −30 to 10° C., or from −20 to 0° C.

The thermochromic pigment microcapsules have a mean diameter that can range from 0.5 to 30 μm, or from 1 to 10 μm, or from 3-5 μm. This mean diameter corresponds to d90 by volume and means that 90% by volume of the microcapsules consists of microcapsules having a size within the indicated range. This mean diameter can be determined by laser granulometry using a Zetasizer Nano ZS device from Malvern Instruments.

The microencapsulation methods used include but are not limited to conventional methods, such as:
chemical processes that are based on the in situ formation of the encapsulating microcapsules, for example through interfacial polymerization or polycondensation, these processes being preferred,
physicochemical processes, for example through phase separation or coacervation, solvent evaporation-extraction, thermal gelation of emulsions (hot melt), or
mechanical processes, for example through nebulization/drying (spray-drying), gelling or freezing drops, or through coating on a fluidized bed (spray-coating).

The thermochromic pigment microcapsules are based on aminoplast resin, on melamine resin, urea resin, or benzoguanamine resin.

The thermochromic pigment microcapsules prepared from melamine resin by means of in situ polymerization.

Another object of the disclosure is an ink composition comprising thermochromic pigment microcapsules.

The thermochromic pigment microcapsules that are present in the ink composition represent from 5 to 50% by weight of the total weight of the ink composition.

Otherwise, the ink composition is composed primarily of water. The water represents 40 to 80% by weight of the total weight of the ink composition.

The ink composition can also contain one or more water-miscible cosolvents. For instance, the ink composition can contain an organic or aqueous solvent, or an aqueous solvent.

Some noteworthy solvents that can be added to the ink composition include water and water-miscible polar solvents, for example:

alcohols: linear or branched $C_1$-$C_{15}$ alcohols such as isopropanol, butanol, isobutanol, pentanol, or benzyl alcohol; glycerin; diglycerin; polyglycerin esters such as ethyl acetate or propyl acetate, carbonate esters such as propylene carbonate or ethylene carbonate, ketones, such as methyl isobutyl ketone (MIBC), acetone, or cyclohexanone, glycols, such as ethylene glycol, diethylene glycol, triethylene glycol, propylene glycol, polyethylene glycol, ethylene glycol monomethyl ether, 3-butylene glycol, and thiodiethylene glycol, amides, such as dimethylacetamide or dimethylformamide, and mixtures thereof.

The solvent or solvents make up 5 to 20% by weight of the total weight of the ink composition.

The ink composition can also contain one or more specific adjuvants which may play different roles depending on the intended end use. These applications may include ink for screen printing, offset printing, gravure printing, powder coating, electrostatic coating, electroplating, roll coating, and inkjet printing, as well as inks for writing instruments such as ballpoint pens, brush pens, markers, and colored pencils. The ink composition can also be added to a thermoplastic or thermosetting resin composition for forming molded parts.

Some noteworthy adjuvants among those mentioned above include:
  rheology modifiers (shear-thinning agents) that are capable of producing a gelling effect, such as xanthan gum or gum arabic,
  defoamers, such as modified aqueous dispersions of polysiloxane (MOUSSEX® from Synthron)
  pH regulators, such as sodium hydroxide, triethanolamine,
  surfactants, such as polyether polyols (TERGITOL™ from DOW),
  biocides, such as isothiazolinones (ACTICIDE® from Thor)
  anticorrosive agents, such as benzotriazole,
  lubricants,
  dispersants,
  coalescing agents,
  crosslinking agents,
  wetting agents,
  plasticizers,
  antioxidants,
  UV stabilizers.

The disclosure further relates to writing instruments comprising an ink composition according to the disclosure. These instruments generally consist of a body containing the ink composition, and possibly a friction element. The writing instrument according is selected from among ballpoint pens, pencils, chalks, and ballpoint pens with friction-erasable ink. The friction element of the writing instrument is preferably a rubber eraser.

The substrates to which the ink composition can be applied are paper, fibers, leather, plastic, glass, metal, wood, and concrete.

In addition to the foregoing, the disclosure also comprises other provisions which will become evident from the description that follows, which relates to the synthesis of compounds of formula (I), characterization thereof, and use thereof as a thermochromic regulating agent in thermochromic pigment compositions.

EXAMPLES

Example 1

Compounds (6), (7), (8), (9), (10), and (11) of the following formulas:

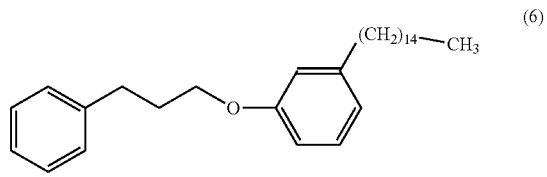

(6)

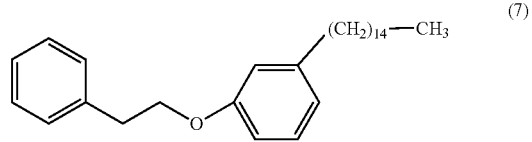

(7)

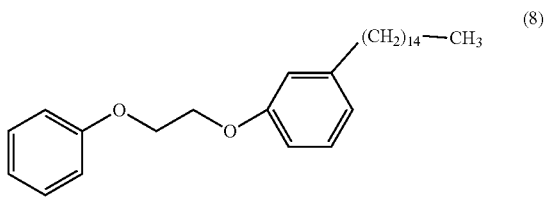

(8)

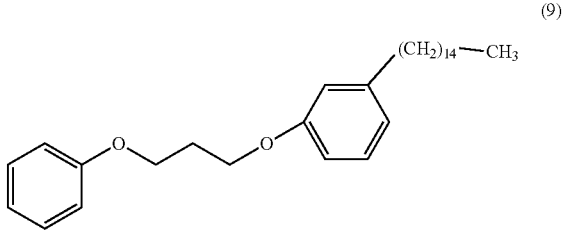

(9)

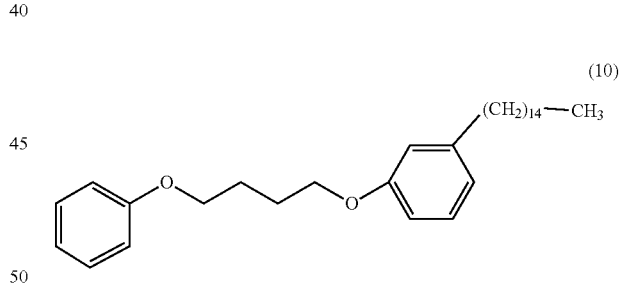

(10)

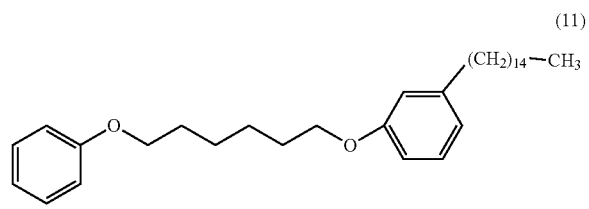

(11)

are prepared:
  Either by solubilization of the reagents in acetonitrile in the presence of potassium carbonate under reflux (85° C.) for 7 days according to the following synthesis scheme:

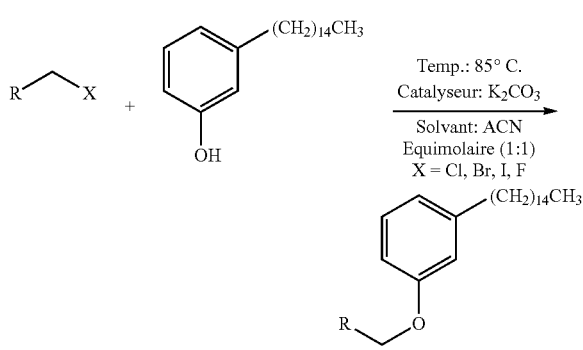

The potassium carbonate is then removed by filtration. Or by solubilization of the reagents in tert-butanol in the presence of sodium hydroxide under reflux (85° C.) for 6 hours according to the following synthesis scheme:

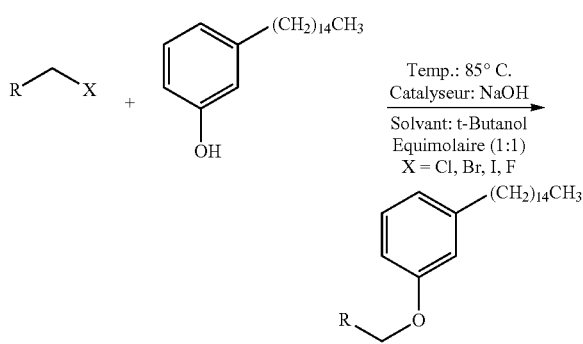

Compounds (6), (7), (8), (9), (10), and (11) synthesized in this manner are purified by successive recrystallizations.

Synthesis of Compound (6)

20 g of 3-pentadecylphenol (CAS no. 501-24-6), 16 g of 1-bromo-3-phenylpropane (CAS no. 637-59-2), and 11 g of calcium carbonate $K_2CO_3$ (CAS no. 584-08-7) are mixed in 100 ml of acetonitrile and then heated under reflux at 85° C. for 7 days.

The potassium carbonate, $K_2CO_3$, is removed by filtration. The acetonitrile is then evaporated, and the solid obtained is recrystallized in 150 ml of ethanol (purity: 95%). The reaction medium is heated under reflux until solubilization is complete, then cooled to room temperature until the product has precipitated. The solid obtained is washed three times with 50 ml of ethanol (purity: 95%).

Gas chromatographic (GPC) analysis of the product obtained using a PerkinElmer Clarus® 680/600S revealed that the product was 96% pure.

Synthesis of Compound (7)

19.7 g of 3-pentadecylphenol (CAS no. 501-24-6) are solubilized in 20 ml of tert-butanol and then heated to 40° C. in order to produce a homogeneous mixture. 3.4 g of sodium hydroxide (CAS no. 1310-73-2) are diluted in 10 ml of distilled water and then added to the reaction medium. After 15 minutes of stirring, 10 g of (2-bromoethyl) benzene (CAS no. 103-63-9) are added to the mixture, and the reaction medium is heated at 80° C. for 6 hours.

The solid product is recovered by recrystallization and filtration and then purified by three successive recrystallizations in 200 ml of ethanol.

Gas chromatographic (GPC) analysis of the product obtained using a PerkinElmer Clarus® 680/600S revealed that the product was 96% pure.

Synthesis of Compound (8)

20 g of 3-pentadecylphenol (CAS no. 501-24-6), 16 g of 0-bromophenetole (CAS no. 637-59-2), and 11 g of calcium carbonate $K_2CO_3$ (CAS no. 584-08-7) are mixed in 100 ml of acetonitrile and then heated under reflux at 85° C. for 7 days.

The potassium carbonate, $K_2CO_3$, is removed by filtration. The acetonitrile is then evaporated, and the solid obtained is recrystallized in 150 ml of ethanol (purity: 95%). The reaction medium is heated under reflux until solubilization is complete, then cooled to room temperature until the product has precipitated. The solid obtained is washed three times with 50 ml of ethanol (purity: 95%).

Gas chromatographic (GPC) analysis of the product obtained using a PerkinElmer Clarus® 680/600S revealed that the product was 99% pure.

Synthesis of Compound (9)

17 g of 3-pentadecylphenol (CAS no. 501-24-6) are solubilized in 100 ml of tert-butanol and then heated to 40° C. in order to produce a homogeneous mixture. 2.9 g of sodium hydroxide (CAS no. 1310-73-2) are diluted in 10 ml of distilled water and then added to the reaction medium. After 15 minutes of stirring, 10 g of 3-phenoxypropyl (CAS no. 588-63-6) are added to the mixture, and the reaction medium is heated at 80° C. for 6 hours.

The solid product is recovered by recrystallization and filtration and then purified by three successive recrystallizations in 150 ml of ethanol.

Gas chromatographic (GPC) analysis of the product obtained using a PerkinElmer Clarus® 680/600S revealed that the product was 99% pure.

Synthesis of Compound (10)

15.8 g of 3-pentadecylphenol (CAS no. 501-24-6) are solubilized in 100 ml of tert-butanol and then heated to 40° C. in order to produce a homogeneous mixture. 2.8 g of sodium hydroxide (CAS no. 1310-73-2) are diluted in 10 ml of distilled water and then added to the reaction medium. After 15 minutes of stirring, 10 g of 4-bromobutyl phenyl ether (CAS no. 1200-03-9) are added to the mixture, and the reaction medium is heated at 80° C. for 6 hours.

The solid product is recovered by recrystallization and filtration and then purified by three successive recrystallizations in 150 ml of ethanol.

Gas chromatographic (GPC) analysis of the product obtained using a PerkinElmer Clarus® 680/600S revealed that the product was 98% pure.

Synthesis of Compound (11)

14 g of 3-pentadecylphenol (CAS no. 501-24-6) are solubilized in 20 ml of tert-butanol and then heated to 40° C. in order to produce a homogeneous mixture. 2.5 g of sodium hydroxide (CAS no. 1310-73-2) are diluted in 10 ml of distilled water and then added to the reaction medium. After 15 minutes of stirring, 10 g of 6-phenoxypropyl (CAS no.

57795-97-2) are added to the mixture, and the reaction medium is heated at 80° C. for 8 hours.

The solid product is recovered by recrystallization and filtration and then purified by three successive recrystallizations in 150 ml of ethanol.

Gas chromatographic (GPC) analysis of the product obtained using a PerkinElmer Clarus® 680/600S revealed that the product was 96% pure.

The melting temperatures $T_{FUS}$ of compounds (6), (7), (8), (9), (10), and (11) obtained were measured by means of differential scanning calorimetry (DSC) using a TA Instruments Q20 apparatus over a temperature range of −50 to 100° C. at heating/cooling rates of +/−20° C./minute. The temperatures measured are shown in table 1 below.

TABLE 1

| Compound of formula (I) | $T_{FUS}$ (° C.) |
|---|---|
| Compound (6) | 35 |
| Compound (7) | 44 |
| Compound (8) | 71 |
| Compound (9) | 56 |
| Compound (10) | 59 |
| Compound (11) | 54 |

Example 2

Compounds (1), (2), (3), (4), (5), (12), (13), (14), (15), and (16) of the following formulas:

(1)
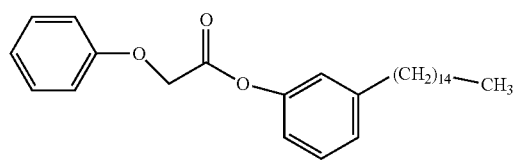

(2)
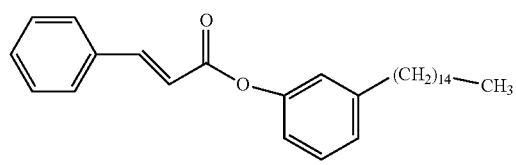

(3)
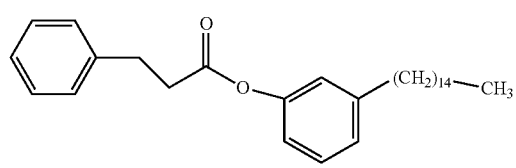

(4)
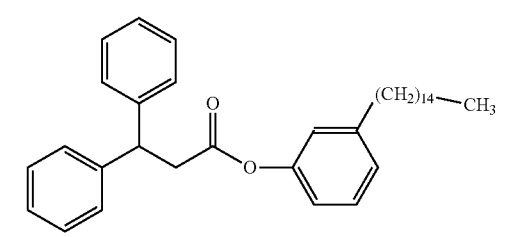

(5)
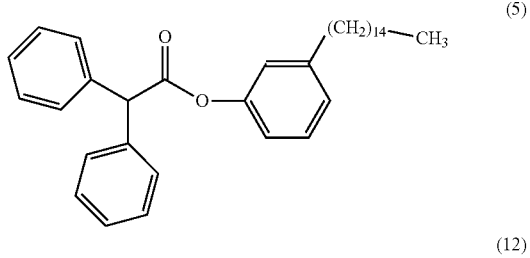

(12)
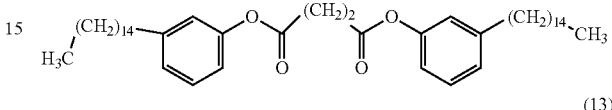

(13)
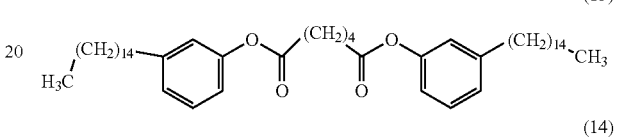

(14)
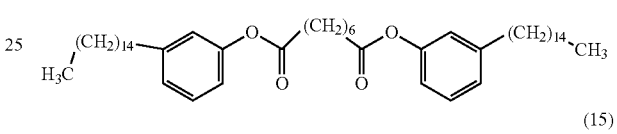

(15)
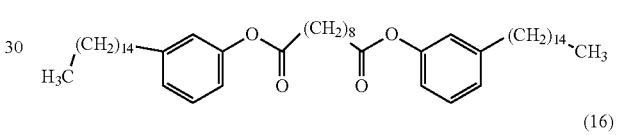

(16)
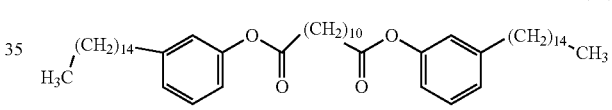

are prepared:
- Either from a carboxylic acid using an alcohol having a melting point below 60° C. as the solvent and para-toluenesulfonic acid as a reaction catalyst. The mixture is heated to a temperature between 120 and 150° C. under a slight vacuum in order to allow for the removal of water and thus a shifting of equilibrium to the synthesis of compounds of formula (I).

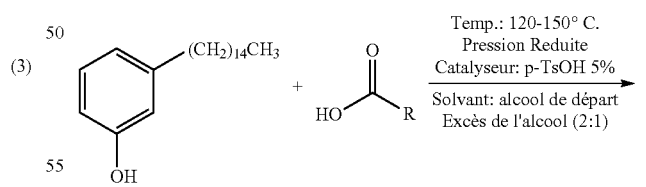

The compounds of formula (I) obtained are purified by recrystallization with a single alcohol.

Either from an alcohol by solubilizing it in tetrahydrofuran (THF) with triethylamine as catalyst at a temperature between 0 and 20° C. The acid chloride is then slowly added dropwise over 30 minutes. The mixture is then reheated to room temperature (25° C.) for 2 hours under stirring.

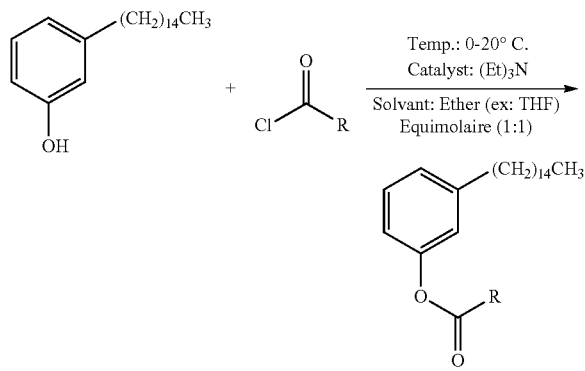

The compounds (1), (2), (3), (4), (5), (12), (13), (14), (15), and (16) obtained are purified by recrystallization.

Synthesis of Compound (1)

17.8 g of 3-pentadecylphenol (CAS no. 501-24-6) and 5.8 g of triethylamine (CAS no. 121-44-8) are solubilized in 250 ml of tetrahydrofuran (CAS no. 109-99-9). The reaction medium is maintained at room temperature and then rendered inert by adding nitrogen. 10 g of phenoxyacetate chloride (CAS no. 701-99-5) are added dropwise for 15 minutes. Once the addition is completed, the reaction medium is stirred for 30 minutes at room temperature.

The reaction medium is then extracted with 100 ml of ethyl acetate. The organic phase is recovered and washed three times with 100 ml of water. The organic phase is then dried over sodium sulfate and the solvent evaporated.

The product is recrystallized twice using isopropanol.

Gas chromatographic (GPC) analysis of the product obtained using a PerkinElmer Clarus® 680/600S revealed that the product was 95% pure.

Synthesis of Compound (2)

18 g of 3-pentadecylphenol (CAS no. 501-24-6) and 6.5 g of triethylamine (CAS no. 121-44-8) are solubilized in 250 ml of tetrahydrofuran (CAS no. 109-99-9). The reaction medium is maintained at room temperature and then rendered inert by adding nitrogen. 10 g of trans-3-phenylacryloyl chloride (CAS no. 102-92-1) diluted in 10 ml of tetrahydrofuran are added dropwise for 15 minutes. Once the addition is completed, the reaction medium is stirred for 30 minutes at room temperature.

The reaction medium is then extracted with 150 ml of ethyl acetate. The organic phase is recovered and washed three times with 150 ml of water. The organic phase is then dried over sodium sulfate and the solvent evaporated.

The product is recrystallized twice using ethanol.

Gas chromatographic (GPC) analysis of the product obtained using a PerkinElmer Clarus® 680/600S revealed that the product was 90% pure.

Synthesis of Compound (3)

20 g of 3-pentadecylphenol (CAS no. 501-24-6), 19.7 g of 3-phenylpropionic acid (CAS no. 501-52-0), and 200 mg of p-toluenesulfonic acid monohydrate (APTS) (CAS no. 6192-52-5) are mixed and heated at 140° C. for 3 days under reduced pressure (400 mbar).

The reaction medium is purified by adding 50 ml of ethanol (purity: 95%) and then heating under reflux until solubilization is complete. The reaction medium is then cooled to room temperature until the product has precipitated. The solid obtained is washed three times with 30 ml of ethanol (purity: 95%).

The product is recrystallized twice using isopropanol.

Gas chromatographic (GPC) analysis of the product obtained using a PerkinElmer Clarus® 680/600S revealed that the product was 83% pure.

Synthesis of Compound (4)

20 g of 3-pentadecylphenol (CAS no. 501-24-6), 30 g of 3,3-diphenylpropionic acid (CAS no. 606-83-7), and 200 mg of p-toluenesulfonic acid monohydrate (APTS) (CAS no. 6192-52-5) are mixed and heated at 160° C. for 3 days under reduced pressure (600 mbar).

The reaction medium is purified by adding 150 ml of ethanol (purity: 95%), then heated to reflux until solubilization is complete. The reaction medium is then cooled to room temperature until the product has precipitated. The solid obtained is washed three times with 30 ml of ethanol (purity: 95%).

Gas chromatographic (GPC) analysis of the product obtained using a PerkinElmer Clarus® 680/600S revealed that the product was 95% pure.

Synthesis of Compound (5)

13.8 g of 3-pentadecylphenol (CAS no. 501-24-6) and 5.0 g of triethylamine (CAS no. 121-44-8) are solubilized in 150 ml of tetrahydrofuran (CAS no. 109-99-9). The reaction medium is maintained at room temperature and rendered inert by adding nitrogen. 10.4 g of diphenylacetyl chloride (CAS no. 1871-76-7) diluted in 15 ml of tetrahydrofuran are added dropwise for 15 minutes. Once the addition is completed, the reaction medium is stirred for 30 minutes at room temperature.

The reaction medium is then extracted with 100 ml of ethyl acetate. The organic phase is recovered and washed three times with 150 ml of water. The organic phase is then dried over sodium sulfate and the solvent evaporated.

The product is recrystallized twice using ethanol cooled to −20° C.

Gas chromatographic (GPC) analysis of the product obtained using a PerkinElmer Clarus® 680/600S revealed that the product was 86% pure.

Synthesis of Compound (12)

38.9 g of 3-pentadecylphenol (CAS no. 501-24-6) and 6.8 g of triethylamine (CAS no. 121-44-8) are solubilized in 250 ml of tetrahydrofuran (CAS no. 109-99-9). The reaction medium is maintained at room temperature and rendered inert by adding nitrogen. 10 g of succinic acid chloride (CAS no. 543-20-4) are added dropwise for 15 minutes. Once the addition is completed, the reaction medium is stirred for 30 minutes at room temperature.

The product obtained is extracted with 100 ml of ethyl acetate. The organic phase is recovered and washed three times with 150 ml of water. The organic phase is then dried over sodium sulfate and the solvent evaporated.

The product is recrystallized twice using isopropanol.

Gas chromatographic (GPC) analysis of the product obtained using a PerkinElmer Clarus® 680/600S revealed that the product was 94% pure.

Synthesis of Compound (13)

33.1 g of 3-pentadecylphenol (CAS no. 501-24-6) and 8.1 g of triethylamine (CAS no. 121-44-8) are solubilized in 250 ml of tetrahydrofuran (CAS no. 109-99-9). The reaction medium is maintained at room temperature and rendered inert by adding nitrogen. 10 g of adipic acid chloride (CAS no. 111-50-2) are added dropwise for 15 minutes. Once the addition is completed, the reaction medium is stirred for 30 minutes at room temperature.

The product obtained is extracted with 100 ml of ethyl acetate. The organic phase is recovered and washed three times with 150 ml of water. The organic phase is then dried over sodium sulfate and the solvent evaporated.

The product is recrystallized twice using isopropanol.

Gas chromatographic (GPC) analysis of the product obtained using a PerkinElmer Clarus® 680/600S revealed that the product was 87% pure.

Synthesis of Compound (14)

15.9 g of 3-pentadecylphenol (CAS no. 501-24-6) and 5.8 g of triethylamine (CAS no. 121-44-8) are solubilized in 250 ml of tetrahydrofuran (CAS no. 109-99-9). The reaction medium is maintained at room temperature and rendered inert by adding nitrogen. 10 g of suberic acid chloride (CAS no. 10027-07-3) are added dropwise for 15 minutes. Once the addition is completed, the reaction medium is stirred for 30 minutes at room temperature.

The product obtained is extracted with 100 ml of ethyl acetate. The organic phase is recovered and washed three times with 150 ml of water. The organic phase is then dried over sodium sulfate and the solvent evaporated.

The product is recrystallized twice using isopropanol.

Gas chromatographic (GPC) analysis of the product obtained using a PerkinElmer Clarus® 680/600S revealed that the product was 96% pure.

Synthesis of Compound (15)

20 g of 3-pentadecylphenol (CAS no. 501-24-6) and 7.2 g of triethylamine (CAS no. 121-44-8) are solubilized in 250 ml of tetrahydrofuran (CAS no. 109-99-9). The reaction medium is cooled to 5° C. and maintained at this temperature in an ice bath. The reaction medium is rendered inert by adding nitrogen. 7.9 g of sebacoyl chloride (CAS no. 111-19-3) are added dropwise for 15 minutes. The reaction medium is then stirred for 2 hours at room temperature.

The product obtained is extracted with 200 ml of ethyl acetate. The organic phase is recovered and washed three times with 100 ml of water. The organic phase is then dried over sodium sulfate and the solvent evaporated.

Gas chromatographic (GPC) analysis of the product obtained using a PerkinElmer Clarus® 680/600S revealed that the product was 90% pure.

Synthesis of Compound (16)

22.7 g of 3-pentadecylphenol (CAS no. 501-24-6) and 8.3 g of triethylamine (CAS no. 121-44-8) are solubilized in 250 ml of tetrahydrofuran (CAS no. 109-99-9). The reaction medium is maintained at room temperature and rendered inert by adding nitrogen. 10 g of lauric acid chloride (CAS no. 4834-98-4) are added dropwise for 15 minutes. Once the addition is completed, the reaction medium is stirred for 30 minutes at room temperature.

The product obtained is extracted with 100 ml of ethyl acetate. The organic phase is recovered and washed three times with 150 ml of water. The organic phase is then dried over sodium sulfate and the solvent evaporated.

The product is recrystallized twice using isopropanol.

Gas chromatographic (GPC) analysis of the product obtained using a PerkinElmer Clarus® 680/600S revealed that the product was 94% pure.

The melting temperatures of compounds (1), (2), (3), (4), (5), (12), (13), (14), (15), and (16) obtained were measured by means of differential scanning calorimetry (DSC) using a TA Instruments Q20 apparatus over a temperature range of −50 to 100° C. at heating/cooling rates of +/−20° C./minute. The temperatures measured are shown in table 2 below.

TABLE 2

| Compound of formula (I) | $T_{FUS}$ (° C.) |
|---|---|
| Compound (1) | 41 |
| Compound (2) | 53 |
| Compound (3) | 43 |
| Compound (4) | 58 |
| Compound (5) | 40 |
| Compound (12) | 53 |
| Compound (13) | 54 |
| Compound (14) | 55 |
| Compound (15) | 55 |
| Compound (16) | 58 |

Example 3

Preparation of a Thermochromic Pigment Composition:

A thermochromic pigment composition is prepared by mixing 2.2 parts by weight of 3-(4-diethylamino-2-ethoxyphenyl)-3-(1-ethyl-2-methylindol-3-yl)-4-azaphthalide (compound (A), CAS no.: 69898-40-4), 2.2 parts by weight of 4,4'-(hexafluoroisopropylidene) diphenol (compound (B1), CAS no.: 1478-61-1), 2.2 parts by weight of 2,2-bis (4-hydroxy-3-methylphenyl)propane (compound (B2), CAS no. 79-97-0), and 93.4 parts by weight of the compound (4) that was synthesized previously (compound (C)). The mixture obtained is heated under stirring at a temperature of 110° C. for 45 minutes until compounds (A), (B1), and (B2) have been completely solubilized in compound (C).

Preparation of Thermochromic Pigment Microcapsules 7.5 parts by weight of an aqueous solution of a copolymer of maleic anhydride and methyl vinyl ether (solution at 33% by weight of copolymer) are neutralized with 9.2 parts by weight of an aqueous solution of sodium hydroxide (1.0 M solution) at pH=4. This solution is diluted with 41.0 parts by weight of water, and the mixture is emulsified with a homogenizer at a speed of at least 15 m·s$^{-1}$. 25.6 parts by weight of the thermochromic pigment composition that was prepared previously are added, and the emulsion obtained is maintained at a temperature of 85° C. for 30 minutes. 16.7 parts by weight of a melamine-formaldehyde prepolymer (50% by weight aqueous solution of prepolymer) are then added to the mixture dropwise. The reaction medium is then heated to a temperature of 90° C. and mixed at a speed of at least 15 m·s$^{-1}$ for 4 hours.

A slurry consisting of microcapsules of thermochromic pigment dispersed in an aqueous solvent is obtained, the microcapsules having a diameter of 4.2 μm d90 as determined using a Zetasizer Nano ZS system from Malvern Instruments with illumination at 632 nm.

The thermochromic pigment microcapsules obtained have the property of changing color from blue to colorless above 58° C. with a hysteresis effect of the color.

Example 4

Preparation of a Thermochromic Pigment Composition

A thermochromic pigment composition is prepared by mixing 3 parts by weight of 3-(4-diethylamino-2-ethoxyphenyl)-3-(1-ethyl-2-methylindol-3-yl)-4-azaphthalide (compound (A), CAS no.: 69898-40-4), 2.5 parts by weight of 4,4'-(hexafluoroisopropylidene) diphenol (compound (B1), CAS no.: 1478-61-1), 2.5 parts by weight of 2,2-bis(4-hydroxy-3-methylphenyl)propane (compound (B2), CAS no. 79-97-0), and 92 parts by weight of compound (8) that was synthesized previously (compound (C)).

The mixture obtained is heated under stirring at a temperature of 110° C. for 1 hour until compounds (A), (B1), and (B2) have been completely solubilized in compound (C).

Preparation of Thermochromic Pigment Microcapsules:

7.5 parts by weight of an aqueous solution of a copolymer of maleic anhydride and methyl vinyl ether (solution at 33% by weight of copolymer) are neutralized with 8.7 parts by weight of an aqueous solution of sodium hydroxide (1.0 M solution) at pH=4. This solution is diluted with 42.6 parts by weight of water, and the mixture is emulsified with a homogenizer at a speed of at least 15 m·s$^{-1}$. 25.2 parts by weight of the thermochromic pigment composition that was prepared previously are added, and the emulsion obtained is maintained at a temperature of 90° C. for 30 minutes. 16.0 parts by weight of a melamine-formaldehyde prepolymer (50% by weight aqueous solution of prepolymer) are then added to the mixture dropwise. The reaction medium is then heated to a temperature of 90° C. and mixed at a speed of at least 15 m·s$^{-1}$ for 4 hours.

A slurry consisting of microcapsules of thermochromic pigment dispersed in an aqueous solvent is obtained, the microcapsules having a diameter of 4.6 μm d90 as determined using a Zetasizer Nano ZS system from Malvern Instruments with illumination at 632 nm.

The thermochromic pigment microcapsules obtained have the property of changing color from blue to colorless above 71° C. with a hysteresis effect of the color.

Example 5

Preparation of a Thermochromic Pigment Composition:

A thermochromic pigment composition is prepared by mixing 2.2 parts by weight of 3-(4-diethylamino-2-ethoxyphenyl)-3-(1-ethyl-2-methylindol-3-yl)-4-azaphthalide (compound (A), CAS no.: 69898-40-4), 2.2 parts by weight of 4,4'-(hexafluoroisopropylidene) diphenol (compound (B1), CAS no.: 1478-61-1), 2.2 parts by weight of 2,2-bis(4-hydroxy-3-methylphenyl)propane (compound (B2), CAS no. 79-97-0), and 93.4 parts by weight of the compound (15) that was synthesized previously (compound (C)).

The mixture obtained is heated under stirring at a temperature of 110° C. for 30 minutes until compounds (A), (B1), and (B2) have been completely solubilized in compound (C).

Preparation of a Microencapsulated Thermochromic Pigment:

7.6 parts by weight of an aqueous solution of a copolymer of maleic anhydride and methyl vinyl ether (solution at 33% by weight of copolymer) are neutralized with 9.4 parts by weight of an aqueous solution of sodium hydroxide (1.0 M solution) at pH=4. This solution is diluted with 39.6 parts by weight of water, and the mixture is emulsified with a homogenizer at a speed of at least 15 m·s$^{-1}$. 26.7 parts by weight of the thermochromic pigment composition that was prepared previously are added, and the emulsion obtained is maintained at a temperature of 80° C. for 30 minutes. 16.7 parts by weight of a melamine-formaldehyde prepolymer (50% by weight aqueous solution of prepolymer) are then added to the mixture dropwise. The reaction medium is then heated to a temperature of 90° C. and mixed at a speed of at least 15 m·s–1 for 4 hours.

A slurry consisting of microcapsules of thermochromic pigment dispersed in an aqueous solvent is obtained, the microcapsules having a diameter of 3.7 μm d90 as determined using a Zetasizer Nano ZS system from Malvern Instruments with illumination at 632 nm.

The thermochromic pigment microcapsules obtained have the property of changing color from blue to colorless above 55° C. with a hysteresis effect of the color.

Preparation of an Ink Composition:

10.8 parts by weight of glycerin (cosolvent) are heated to a temperature of 30° C. under stirring with a paddle. 0.2 parts by weight of benzotriazole (anticorrosive) and 0.2 parts by weight of an aqueous solution comprising 2.5% by weight of 1,2-benzisothiazolin-3-one and 2.5% by weight of 2-methyl-4-isothiazolin-3-one (biocide), 0.5 parts by weight of an aqueous dispersion of a polysiloxane copolymer (aqueous dispersion at 50% by weight of polymer) (antifoam), and 0.5 parts by weight of a polyether polyol (surfactant) are then added. The mixture is stirred until the additives have been completely solubilized. 0.5 part by weight of xanthan gum (rheology modifier) is added slowly for 15 minutes. After dispersion of the rheology modifier, 26.8 parts by weight of distilled water are added. The ink composition obtained is stirred for 3 hours, whereupon 60 parts by weight of an aqueous dispersion of thermochromic pigment microcapsules that was prepared above (aqueous dispersion 30% by weight of thermochromic pigment microcapsules) are added. The pH of the ink composition is adjusted to pH=8 with 0.5 parts by weight of triethanolamine. The blue ink is then dispersed with a disperser at a speed of at least 15 m·s$^{-1}$ for 30 minutes. The ink composition is degassed under reduced pressure prior to injection into ink cartridges.

Example 6

Preparation of a Thermochromic Pigment Composition:

A thermochromic pigment composition is prepared by mixing 2.3 parts by weight of 3-(4-diethylamino-2-ethoxyphenyl)-3-(1-ethyl-2-methylindol-3-yl)-4-azaphthalide (compound (A), CAS no.: 69898-40-4), 1.9 parts by weight of 4,4'-(hexafluoroisopropylidene) diphenol (compound (B1), CAS no.: 1478-61-1), 1.9 parts by weight of 2,2-bis(4-hydroxy-3-methylphenyl)propane (compound (B2), CAS no.: 79-97-0), and 93.9 parts by weight of compound (2) that was synthesized previously (compound (C)). The mixture obtained is heated under stirring at a temperature of 110° C. for 45 minutes until compounds (A), (B1), and (B2) have been completely solubilized in compound (C).

Preparation of Thermochromic Pigment Microcapsules:

9.3 parts by weight of an aqueous solution of a copolymer of maleic anhydride and methyl vinyl ether (solution at 27% by weight of copolymer) are neutralized with 16.3 parts by weight of an aqueous solution of sodium hydroxide (1.0 M solution) at pH=4.5. This solution is diluted with 27.6 parts by weight of water, and the mixture is emulsified with a homogenizer at a rate of at least 15 m·s$^{-1}$. 27.0 parts by weight of the previously prepared thermochromic pigment composition are added, and the emulsion obtained is maintained at a temperature of 85° C. for 30 minutes. 19.8 parts by weight of a melamine-formaldehyde prepolymer (50% by weight aqueous solution of prepolymer) are then added to the mixture dropwise. The reaction medium is then heated to a temperature of 90° C. and mixed at a speed of at least 15 m·s$^{-1}$ for 4 hours.

A slurry consisting of microcapsules of thermochromic pigment dispersed in an aqueous solvent is obtained, the microcapsules having a diameter of 2.8 μm d90 as determined using a Zetasizer Nano ZS system from Malvern Instruments with illumination at 632 nm.

The thermochromic pigment microcapsules obtained have the property of changing color from blue to colorless above 54° C. with a hysteresis effect of the color.

Preparation of an Ink Composition:

10.5 parts by weight of glycerin (cosolvent) are heated to a temperature of 30° C. under stirring with a paddle. 0.2 parts by weight of benzotriazole (anticorrosive) and 0.2 parts by weight of an aqueous solution comprising 2.5% by weight of 1,2-benzisothiazolin-3-one and 2.5% by weight of 2-methyl-4-isothiazolin-3-one (biocide), 0.5 parts by weight of an aqueous dispersion of a polysiloxane copolymer (aqueous dispersion at 50% by weight of polymer) (antifoam), and 0.8 parts by weight of a diester sulfosuccinate (surfactant) are then added. The mixture is stirred until the additives have been completely solubilized. 0.5 parts by weight of xanthan gum (rheology modifier) is added slowly for 15 minutes. After dispersion of the rheology modifier, 26.8 parts by weight of distilled water are added. The ink composition obtained is stirred for 3 hours, whereupon 60 parts by weight of an aqueous dispersion of thermochromic pigment microcapsules that was prepared above (aqueous dispersion 30% by weight of thermochromic pigment microcapsules) are added. The pH of the ink composition is adjusted to pH=8 with 0.5 parts by weight of triethanolamine. The blue ink is then dispersed with a disperser at a speed of at least 15 m·s$^{-1}$ for 30 minutes. The ink composition is degassed under reduced pressure prior to injection into cartridges.

Example 7

Preparation of a Thermochromic Pigment Composition:

A thermochromic pigment composition is prepared by mixing 2.2 parts by weight of 3-(4-diethylamino-2-ethoxyphenyl)-3-(1-ethyl-2-methylindol-3-yl)-4-azaphthalide (compound (A), CAS no.: 69898-40-4), 2.0 parts by weight of 4,4'-(hexafluoroisopropylidene)diphenol (compound (B1), CAS no.: 1478-61-1), 2.0 parts by weight of 2,2-bis(4-hydroxy-3-methylphenyl)propane (compound (B2), CAS no. 79-97-0), and 93.8 parts by weight of compound (9) that was synthesized previously (compound (C)). The mixture obtained is heated under stirring at a temperature of 110° C. for 45 minutes until compounds (A), (B1), and (B2) have been completely solubilized in compound (C).

Preparation of Thermochromic Pigment Microcapsules:

9.0 parts by weight of an aqueous solution of a copolymer of maleic anhydride and methyl vinyl ether (solution at 27% by weight of copolymer) are neutralized with 15.7 parts by weight of an aqueous solution of sodium hydroxide (1.0 M solution) at pH=4.5. This solution is diluted with 28.1 parts by weight of water, and the mixture is emulsified with a homogenizer at a rate of at least 15 m·s$^{-1}$. 28.1 parts by weight of the previously prepared thermochromic pigment composition are added, and the emulsion obtained is maintained at a temperature of 85° C. for 30 minutes. 19.1 parts by weight of a melamine-formaldehyde prepolymer (50% by weight aqueous solution of prepolymer) are then added to the mixture dropwise. The reaction medium is then heated to a temperature of 90° C. and mixed at a speed of at least 15 m·s−1 for 4 hours.

A slurry consisting of microcapsules of thermochromic pigment dispersed in an aqueous solvent is obtained, the microcapsules having a diameter of 4.2 μm d90 as determined using a Zetasizer Nano ZS system from Malvern Instruments with illumination at 632 nm.

The thermochromic pigment microcapsules obtained have the property of changing color from blue to colorless above 56° C. with a hysteresis effect of the color.

Example 8

Preparation of a Thermochromic Pigment Composition:

A thermochromic pigment composition is prepared by mixing 2.2 parts by weight of 3-(4-diethylamino-2-ethoxyphenyl)-3-(1-ethyl-2-methylindol-3-yl)-4-azaphthalide (compound (A), CAS no.: 69898-40-4), 2.0 parts by weight of 4,4'-(hexafluoroisopropylidene)diphenol (compound (B1), CAS no.: 1478-61-1), 2.0 parts by weight of 2,2-bis (4-hydroxy-3-methylphenyl)propane (compound (B2), CAS no. 79-97-0), and 93.8 parts by weight of compound (14) that was synthesized previously (compound (C)). The mixture obtained is heated under stirring at a temperature of 110° C. for 45 minutes until compounds (A), (B1), and (B2) have been completely solubilized in compound (C).

Preparation of Thermochromic Pigment Microcapsules:

9.4 parts by weight of an aqueous solution of a copolymer of maleic anhydride and methyl vinyl ether (solution at 27% by weight of copolymer) are neutralized with 16.2 parts by weight of an aqueous solution of sodium hydroxide (1.0 M solution) at pH=4.5. This solution is diluted with 27.5 parts by weight of water, and the mixture is emulsified with a homogenizer at a rate of at least 15 m·s$^{-1}$. 27.3 parts by weight of the previously prepared thermochromic pigment composition are added, and the emulsion obtained is maintained at a temperature of 85° C. for 30 minutes. 19.6 parts by weight of a melamine-formaldehyde prepolymer (50% by weight aqueous solution of prepolymer) are then added to the mixture dropwise. The reaction medium is then heated to a temperature of 90° C. and mixed at a speed of at least 15 m·s−1 for 4 hours.

A slurry consisting of microcapsules of thermochromic pigment dispersed in an aqueous solvent is obtained, the microcapsules having a diameter of 3.2 μm d90 as determined using a Zetasizer Nano ZS system from Malvern Instruments with illumination at 632 nm.

The thermochromic pigment microcapsules obtained have the property of changing color from blue to colorless above 55° C. with a hysteresis effect of the color.

Preparation of an Ink Composition:

10.3 parts by weight of glycerine (cosolvent) are heated to a temperature of 30° C. under stirring with a paddle. 0.2 parts by weight of benzotriazole (anticorrosive) and 0.2 parts by weight of an aqueous solution comprising 2.5% by weight of 1,2-benzisothiazolin-3-one and 2.5% by weight of 2-methyl-4-isothiazolin-3-one (biocide), 0.5 parts by weight of an aqueous dispersion of a polysiloxane copolymer (aqueous dispersion at 50% by weight of polymer) (antifoam), and 0.5 parts by weight of a polyether polyol (surfactant) are then added. The mixture is stirred until the additives have been completely solubilized. 0.5 part by weight of xanthan gum (rheology modifier) is added slowly for 15 minutes. After dispersion of the rheology modifier, 26.8 parts by weight of distilled water are added. The ink composition obtained is stirred for 3 hours, whereupon 60 parts by weight of an aqueous dispersion of thermochromic pigment microcapsules that was prepared above (aqueous dispersion 30% by weight of thermochromic pigment microcapsules) are added. The pH of the ink composition is adjusted to pH=8 with 1 part by weight of NaOH. The blue ink is then dispersed with a disperser at a speed of at least 15 m·s$^{-1}$ for 30 minutes. The ink composition is degassed under reduced pressure prior to injection into ink cartridges.

Example 9

Preparation of a Thermochromic Pigment Composition:

A thermochromic pigment composition is prepared by mixing 2.2 parts by weight of 3-(4-diethylamino-2-ethoxyphenyl)-3-(1-ethyl-2-methylindol-3-yl)-4-azaphthalide (compound (A), CAS no.: 69898-40-4), 2.0 parts by weight of 4,4'-(hexafluoroisopropylidene)diphenol (compound (B1), CAS no.: 1478-61-1), 2.0 parts by weight of 2,2-bis (4-hydroxy-3-methylphenyl)propane (compound (B2), CAS no. 79-97-0), and 93.8 parts by weight of compound (16) that was synthesized previously (compound (C)). The mixture obtained is heated under stirring at a temperature of 110° C. for 45 minutes until compounds (A), (B1), and (B2) have been completely solubilized in compound (C).

Preparation of Thermochromic Pigment Microcapsules:

9.3 parts by weight of an aqueous solution of a copolymer of maleic anhydride and methyl vinyl ether (solution at 27% by weight of copolymer) are neutralized with 16.0 parts by weight of an aqueous solution of sodium hydroxide (1.0 M solution) at pH=4.5. This solution is diluted with 27.7 parts by weight of water, and the mixture is emulsified with a homogenizer at a rate of at least 15 m·s$^{-1}$. 27.1 parts by weight of the previously prepared thermochromic pigment composition are added, and the emulsion obtained is maintained at a temperature of 85° C. for 30 minutes. 19.9 parts by weight of a melamine-formaldehyde prepolymer (50% by weight aqueous solution of prepolymer) are then added to the mixture dropwise. The reaction medium is then heated to a temperature of 90° C. and mixed at a speed of at least 15 m·s$^{-1}$ for 4 hours.

A slurry consisting of microcapsules of thermochromic pigment dispersed in an aqueous solvent is obtained, the microcapsules having a diameter of 3.1 µm d90 as determined using a Zetasizer Nano ZS system from Malvern Instruments with illumination at 632 nm.

The thermochromic pigment microcapsules obtained have the property of changing color from blue to colorless above 58° C. with a hysteresis effect of the color.

Determination of the Discoloration and Recoloration Temperatures of the Thermochromic Pigment Microcapsules Prepared in Examples 3, 4, 5, 6, 7, 8, and 9:

The transition temperatures of thermochromic pigment microcapsules obtained were measured by means of differential scanning calorimetry (DSC) using a TA Instruments Q20 apparatus over a temperature range of −50 to 100° C. at heating/cooling rates of +/−20° C./minute. The temperatures measured are shown in table 3 below.

TABLE 3

Transition temperatures of the thermochromic pigment microcapsules prepared in examples 3, 4, 5, 6, 7, 8, and 9

| | Color change colored ↔ colorless | T1 (° C.) | T2 (° C.) | T3 (° C.) | T4 (° C.) | $T_H$ (° C.) | $T_G$ (° C.) | ΔH |
|---|---|---|---|---|---|---|---|---|
| Thermochromic pigment microcapsules comprising compound (4) (example 3) | blue ↔ colorless | −20 | −10 | 48 | 58 | −15 | 53 | 68 |
| Thermochromic pigment microcapsules comprising compound (8) (example 4) | blue ↔ colorless | 0 | 10 | 55 | 71 | 5 | 63 | 58 |
| Thermochromic pigment microcapsules comprising compound (15) (example 5) | blue ↔ colorless | −5 | 5 | 40 | 55 | 0 | 48 | 48 |
| Thermochromic pigment microcapsules comprising compound (2) (example 6) | blue ↔ colorless | −8 | −5 | 40 | 54 | −7 | 47 | 54 |

TABLE 3-continued

Transition temperatures of the thermochromic pigment microcapsules prepared in examples 3, 4, 5, 6, 7, 8, and 9

| | Color change colored ↔ colorless | T1 (° C.) | T2 (° C.) | T3 (° C.) | T4 (° C.) | $T_H$ (° C.) | $T_G$ (° C.) | ΔH |
|---|---|---|---|---|---|---|---|---|
| Thermochromic pigment microcapsules comprising compound (9) (example 7) | blue ↔ colorless | −7 | 18 | 38 | 56 | 6 | 47 | 41 |
| Thermochromic pigment microcapsules comprising compound (14) (example 8) | blue ↔ colorless | 5 | 10 | 35 | 55 | 8 | 45 | 37 |
| Thermochromic pigment microcapsules comprising compound (16) (example 9) | blue ↔ colorless | 8 | 12 | 36 | 58 | 10 | 47 | 37 |

The transition temperatures measured are as follows:
T1: temperature of complete recoloration,
T2: temperature of partial recoloration,
T3: temperature of partial discoloration,
T4: temperature of complete discoloration, $$T_H = \frac{T1 + T2}{2},$$

$$T_G = \frac{T3 + T4}{2},$$

ΔH = hysteresis range = $T_G - T_H$.

The invention claimed is:

1. A thermochromic pigment composition, comprising:
(A) at least one organic electron-donating dye compound,
(B) at least one electron-accepting compound, and
at least one compound of formula (I):

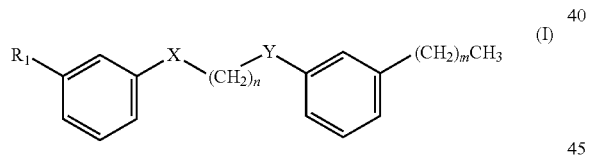

in which:
X represents $CHR_2$, O, OCO, or CH=CH,
Y represents O or COO,
$R_1$ represents H or $(CH_2)_pCH_3$,
$R_2$ represents a phenyl group or H,
m=12-18,
n=0-14,
p=12-18, and
on the condition that, if n=0, X represents $CHR_2$ or CH=CH.

2. The thermochromic pigment composition according to claim 1, corresponding to the following formula ($I_a$):

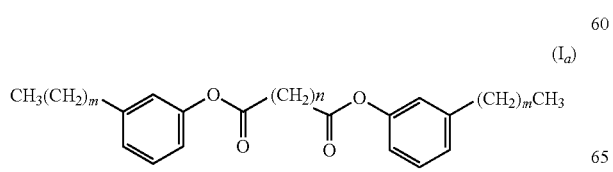

in which:
m=12-18, and
n=1-14.

3. The thermochromic pigment composition according to claim 1, corresponding to the following formula ($I_b$):

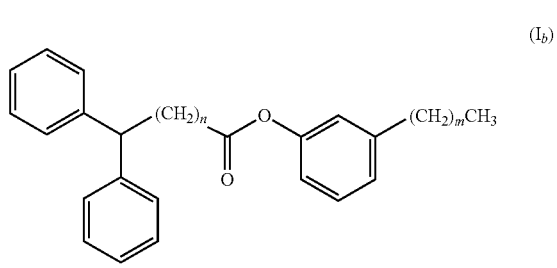

in which:
m=12-18, and
n=0-14.

4. The thermochromic pigment composition according to claim 1, corresponding to the following formula ($I_c$):

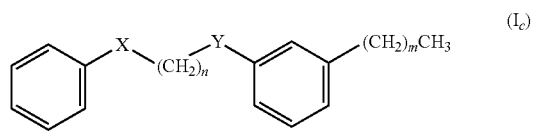

in which:
X represents $CH_2$, or O,
Y represents O or COO, m=12-18, and n=1-14.

5. The thermochromic pigment composition according to claim 1, wherein the at least one compound of formula (I) is selected from the group consisting of

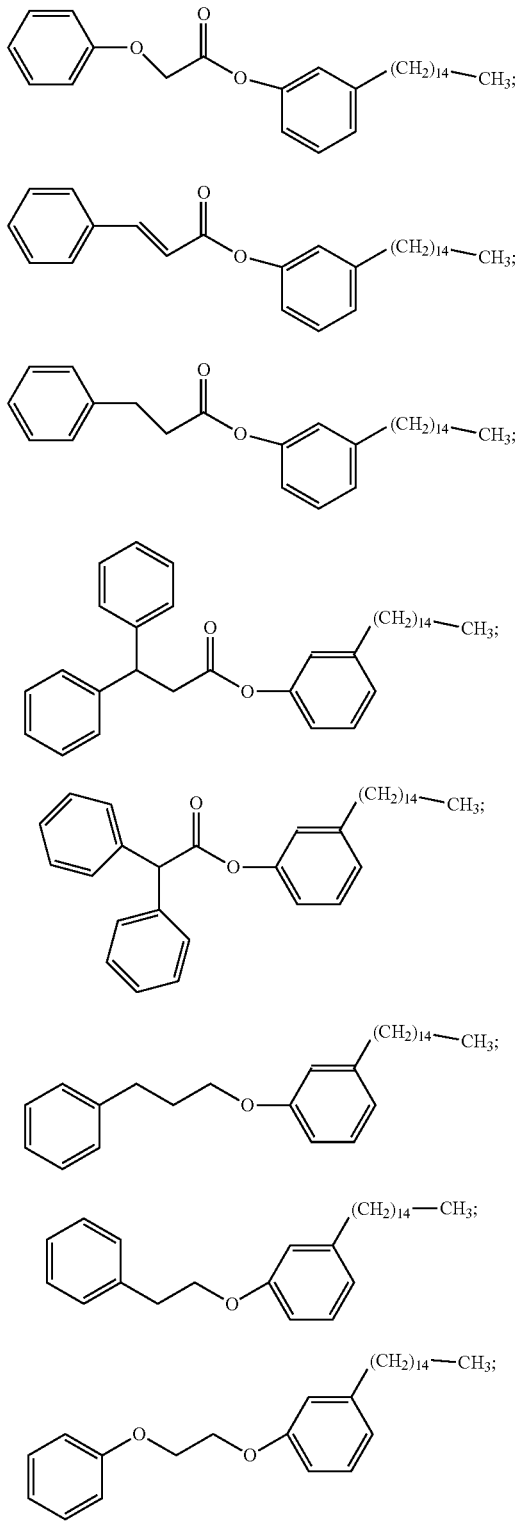

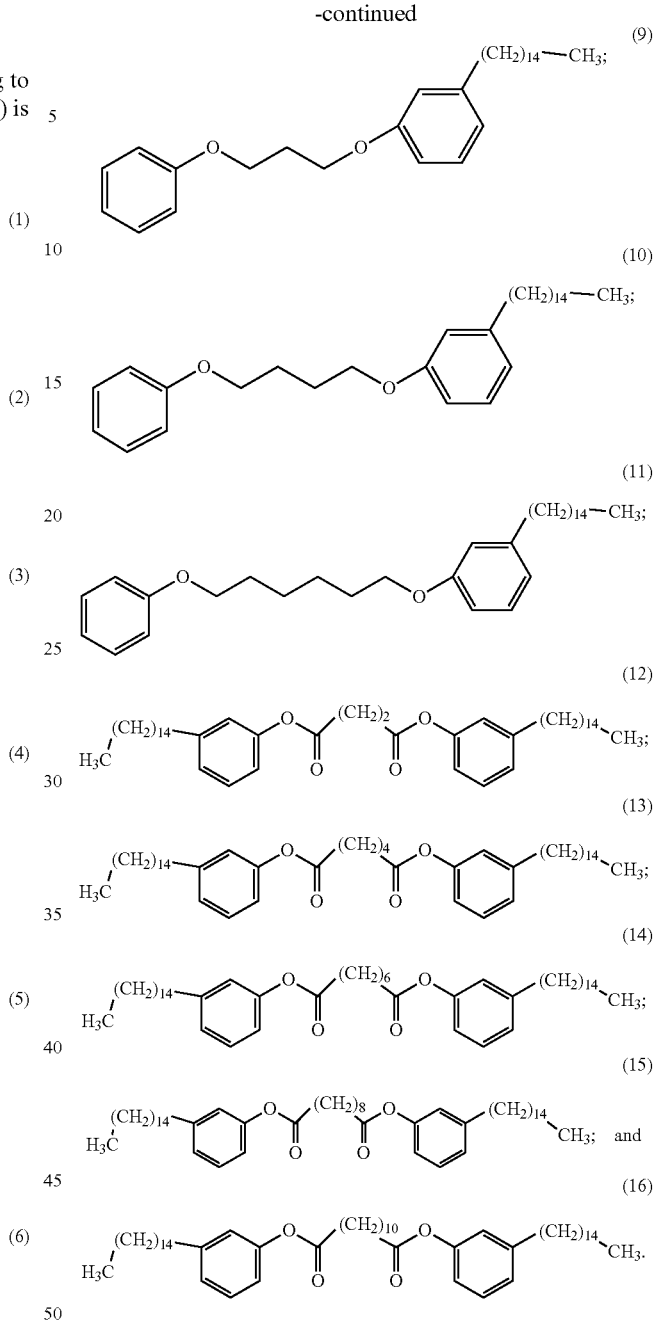

6. The thermochromic pigment composition according to claim 1, wherein compound (A) is selected from the group consisting of 3-(4-diethylamino-2-ethoxyphenyl)-3-(1-ethyl-2-methylindol-3-yl)-4-azaphthalide (Blue 63, CAS no.: 69898-40-4), 2'-(dibenzylamino)-6'-(diethylamino) fluorane (CAS no.: 34372-72-0), N,N-dimethyl-4-[2-[2-(octyloxy)phenyl]-6-phenyl-4-pyridinyl]benzenamine (Yellow CK37, CAS no.: 144190-25-0), 7-(4-diethylamino-2-hexyloxyphenyl)-7-(1-ethyl-2-methyl-1H-indol-3-yl)-7H-furo[3,4-b]pyridine-5-one (Blue 203, CAS no.: 98660-18-5), 2-(2,4-dimethylphenylamino)-3-methyl-6-diethylaminofluoran (Black 15, CAS no.: 36431-22-8), and 3,3-bis-(1-butyl-2-methyl-indol-3-yl)-3H-isobenzofuran-1-one (Red 40, CAS no.: 50292-91-6).

7. The thermochromic pigment composition according to claim 1, wherein compound (B) is selected from the group consisting of 2,2-bis (4-hydroxy-3-methylphenyl)propane (Bisphenol C, CAS no.: 79-97-0), 4-hexyl-1,3-dihydroxybenzene (4-hexylresorcinol, CAS no.: 136-77-6), 4,4'-cyclohexylidenebisphenol (BPZ, CAS no.: 843-55-0), 4,4'-(hexafluoroisopropylidene)diphenol (Bisphenol AF, CAS no.: 1478-61-1), 4,4'-(1-phenylethylidene)bisphenol (CAS no.: 1571-75-1), 2,2'-dihydroxybiphenyl (CAS no.: 1806-29-7), 4,4'-(1,4-phenylenediisopropylidene)bisphenol (CAS no.: 2167-51-3), 1,1-bis(4-hydroxy-3-methylphenyl)cyclohexane (CAS no.: 2362-14-3), 9,9-bis(4-hydroxyphenyl)fluorene (CAS no.: 3236-71-3), 4,4'-(1,3-phenylenediisopropylidene)bisphenol (CAS no.: 13595-25-0), 1,1,1-tris(4-hydroxyphenyl)ethane (CAS no.: 27955-94-8), 4,4'-(2-ethylhexylidene)diphenol (CAS no.: 74462-02-5), α,α,α'-tris(4-hydroxyphenyl)-1-ethyl-4-isopropylbenzene (CAS no.: 110726-28-8).

8. A thermochromic pigment microcapsule comprising a composition according to 1.

9. An ink composition comprising a thermochromic pigment microcapsules according to claim 8.

10. A writing instrument comprising an ink composition according to claim 9.

11. The writing instrument according to claim 10, wherein the ink is erasable and the writing instrument is a ballpoint pen with an eraser.

12. A compound selected from the group consisting of (1)
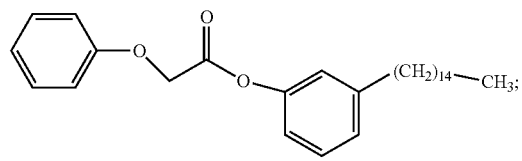

(2)
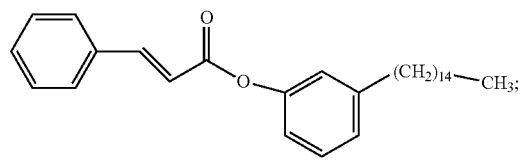

(3)
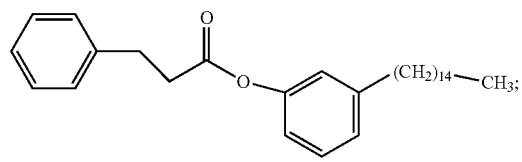

(4)

(5)
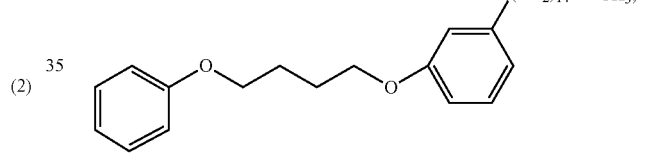

-continued (6)
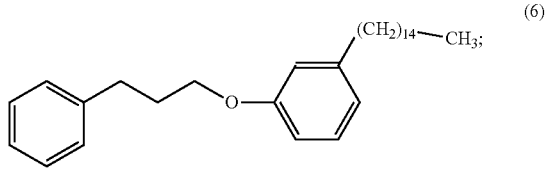

(7)
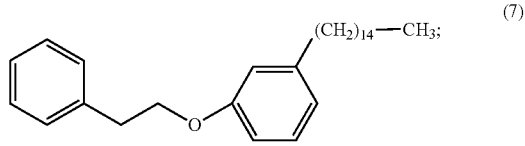

(8)
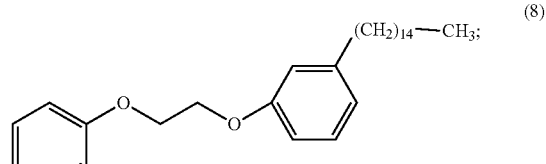

(9)
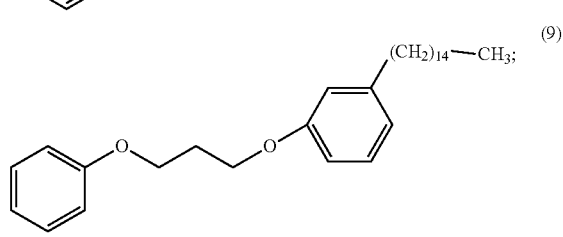

(10)
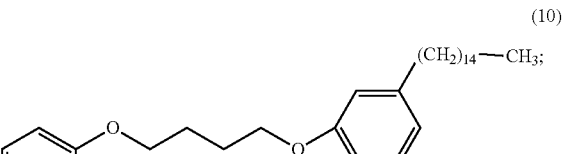

(11)

(12)
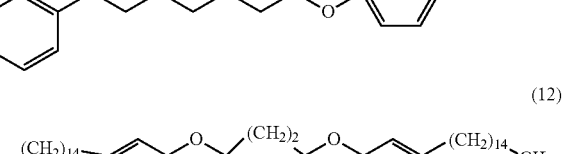

(13)
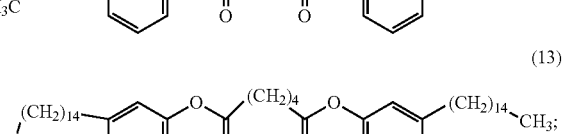

(14)
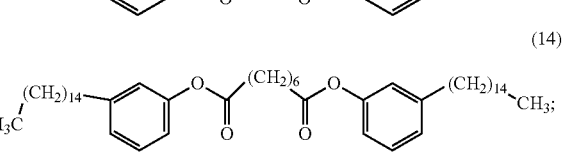

(15)
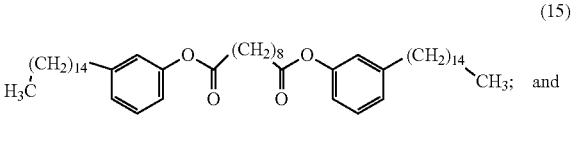 and

-continued
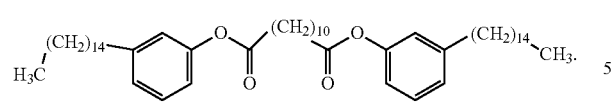
(16)
* * * * *